United States Patent
Nappholz

(10) Patent No.: US 6,421,555 B1
(45) Date of Patent: Jul. 16, 2002

(54) METHOD AND APPARATUS FOR DISCRIMINATING BETWEEN ELECTROMAGNETIC INTERFERENCE SIGNALS AND ELECTROMEDICAL SCANNING SIGNALS, PARTICULARLY OF CARDIOLOGICAL IMPLANTS

(75) Inventor: Tibor Nappholz, Evergreen, CO (US)

(73) Assignee: Biotronik Mess-und Therapiegeräte GmbH & Co. Ingenieurbüro Berlin, Berlin (DE)

( * ) Notice: Subject to any disclaimer, the term of this patent is extended or adjusted under 35 U.S.C. 154(b) by 203 days.

(21) Appl. No.: 09/595,022

(22) Filed: Jun. 16, 2000

(30) Foreign Application Priority Data

Jun. 17, 1999  (DE) .......................... 199 27 616

(51) Int. Cl.[7] .......................... A61B 5/0428; A61B 5/04; A61N 1/16
(52) U.S. Cl. .............................. 600/509; 607/2; 607/5; 607/9
(58) Field of Search ................ 607/2, 5, 6, 9; 600/509

(56) References Cited

U.S. PATENT DOCUMENTS

| 5,265,601 | A | * | 11/1993 | Mehra | 607/9 |
|---|---|---|---|---|---|
| 5,336,242 | A | | 8/1994 | Zadeh | 607/11 |
| 5,500,006 | A | | 3/1996 | Heinze | 607/24 |
| 5,871,509 | A | | 2/1999 | Noren | 607/9 |
| 5,873,894 | A | * | 2/1999 | Vandegriff et al. | 607/9 |
| 5,891,171 | A | | 4/1999 | Wickham | 607/4 |
| 5,897,575 | A | | 4/1999 | Wickham | 607/4 |
| 6,112,119 | A | * | 8/2000 | Schuelke et al. | 607/9 |
| 6,188,926 | B1 | * | 2/2001 | Vock | 607/9 |

FOREIGN PATENT DOCUMENTS

| DE | 9105912.7 | 11/1991 | ............ A61N/1/37 |
|---|---|---|---|
| DE | 4111505 | 10/1992 | ............ A61N/1/365 |
| DE | 4444144 | 6/1996 | ............ A61N/1/365 |

* cited by examiner

Primary Examiner—Carl Layno
(74) Attorney, Agent, or Firm—Browdy and Neimark

(57) ABSTRACT

A method for discriminating between externally-radiated, electromagnetic interference signals and electromedical scanning signals comprises the following steps: the preamplification of the scanning signals by means of two preamplifiers; the comparison of the preamplified scanning signals by a comparator; the phase-sensitive evaluation of the comparator output signal for differentiating between scanning signals and interference signals; the feedback of the comparator output signal to the amplification control of the preamplifiers such that the comparator output signal is minimized when an interference signal is detected.

4 Claims, 1 Drawing Sheet

METHOD AND APPARATUS FOR DISCRIMINATING BETWEEN ELECTROMAGNETIC INTERFERENCE SIGNALS AND ELECTROMEDICAL SCANNING SIGNALS, PARTICULARLY OF CARDIOLOGICAL IMPLANTS

BACKGROUND OF THE INVENTION

1. Field of the Invention

The invention relates to a method and an apparatus for discriminating between electromagnetic interference signals that are beamed in externally and electromedical scanning signals, particularly in input signals of cardiological implants such as cardiac pacemakers, defibrillators and the like, in neurological stimulus detection, etc.

2. Background Art

The problem to be addressed by the invention is the increasing "poisoning" of our environment with electromagnetic radiation from a wide variety of sources. All electronic devices, particularly cardiological implants, are exposed to numerous different environmental electromagnetic interferences (EMIs). This problem has been exacerbated by the dramatic increase in EMI signal sources, such as alarm systems, anti-theft systems, mobile telephones, etc., and the heightened sensitivity of modern electromedical devices for example, modern cardiological implants detect and assess extremely small signals in order to diagnose the actual status of the heart as accurately as possible and, based on this assessment, generate the optimum therapeutic pulses for the dysfunctional heart. Merely shielding the implant with a metal housing is inadequate, because interference signals can be radiated in via the connected signal lines and their inputs on the implant.

To remedy this situation, it is known from the prior art to provide special lead-throughs for the implant connections, which, however, are only sufficiently effective for very high frequencies, such as those used in mobile telephones. Lower frequencies, such as are generated by, for example, alarm or anti-theft systems, mains frequencies and other industrial sources of interference signals, cannot be shielded as well as higher frequencies, and represent the primary threats to the proper function of the implant.

In this connection, a further proposal is the use of bipolar supply lines and electrodes, which at least reduce the level of interferences. These types of signal lines also cannot completely eliminate interferences, however.

Finally, it is known from the prior art, for example U.S. Pat. Nos. 5,292,348, 5,817,134 or U.S. Pat. No. 5,857,977 to identify and distinguish different tachycardia through the detection of the time of the occurrence of signals at two electrode poles. Complicated evaluation algorithms such as the cross-phase spectrum or the cross-correlation of the signals are used here.

SUMMARY OF THE INVENTION

Based on the outlined problem, it is the object of the invention to provide a method of discriminating interferences between EMI interference signals and actual scanning signals, e.g., of cardiological implants, the method being especially simple to implement.

In accordance with the invention, this object is accomplished by a method of discriminating between externally-radiated EMI interference signals and electromedical scanning signals, particularly in input signals of cardiological implants, comprising the following steps:

the preamplification of the scanning signals by means of two preamplifiers;

the comparison of the preamplified scanning signals by a comparator;

the phase-sensitive evaluation of the comparator output signal for differentiating between scanning signals and EMI interference signals;

the feedback of the comparator output signal to an amplification control of the preamplifiers such that the comparator output signal is minimized when an interference signal is detected.

The foundation of the invention is the recognition that the EMI interference signals, particularly with respect to bipolar scanning electrodes that are used in cardiological implants, are far-field signals whose magnitude is a function of the spacing between the two electrodes. In telecommunications terminology, this spacing can be understood as the "dipole spacing" between the two electrodes.

In contrast to EMI interference signals, the scanning signal, that is, the cardiological signal detected by the bipolar electrode of a cardiac pacemaker, is a near-field signal, which is independent of the dipole spacing. The cardiological near-field signal originates from, for example, the electrical ventricular stimulus conduction successively passing the bipolar electrodes. The two electrodes of the bipolar arrangement are charged with different potentials at a specific time. The near-field signals at the two electrodes are therefore not in phase.

The invention capitalizes on the above-described difference between near and far fields. EMI interference signals from a specific source occur, for example, as two in-phase signals of different amplitudes at the two bipolar electrodes of a pacemaker. This difference in amplitudes actually generates the interference signal, which is registered as an interference by the scanning-and-evaluation circuit of an implant.

The method of the invention and the corresponding apparatus, which are described in the ensuing description of an exemplary embodiment in conjunction with the attached drawing, are provided for eliminating this problem.

DESCRIPTION OF THE PREFERRED EMBODIMENT

Figure 1:
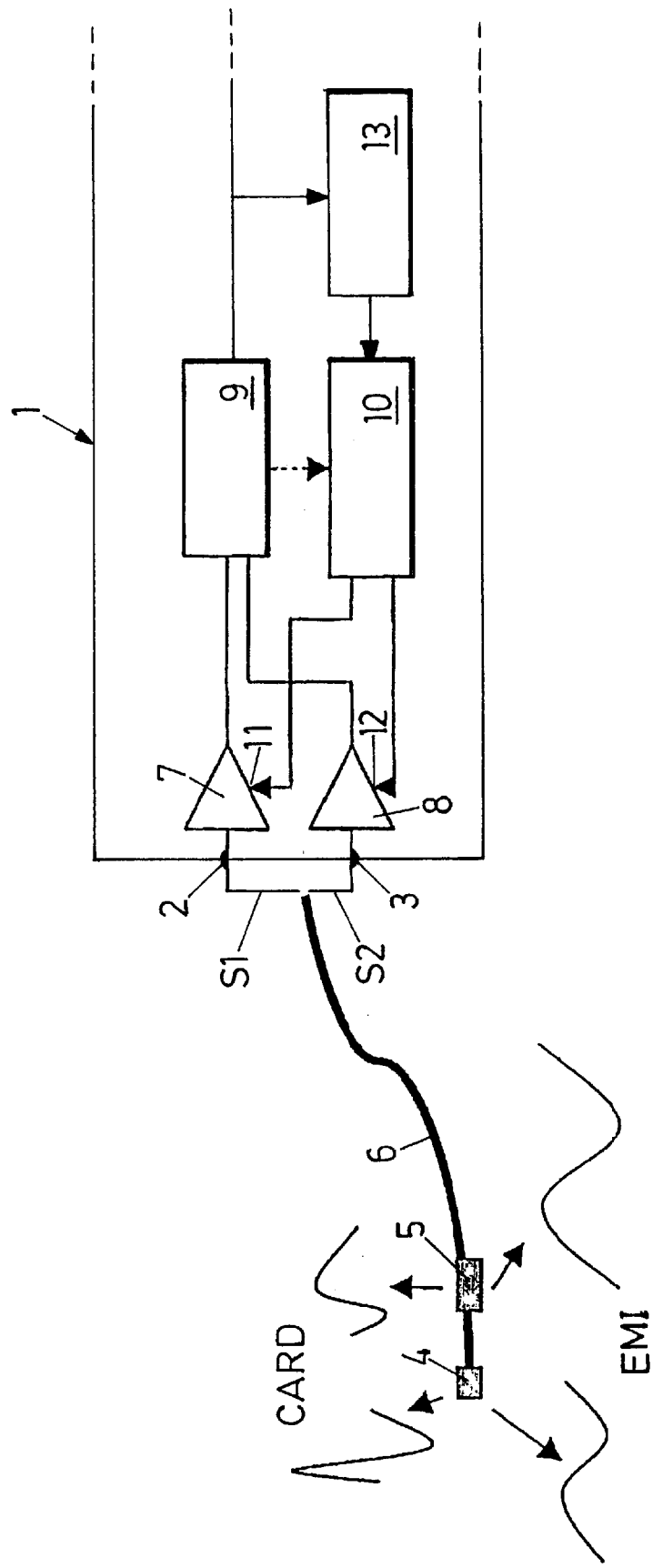
FIG. 1 is a relatively schematic diagram of an apparatus for discriminating between externally-radiated, electromagnetic interference signals and bipolar scanning signals in input signals of cardiological implants.

In the drawing, 1 indicates a part of a defibrillator, in which a differential or discrimination circuit, to be described in detail below, is provided on the input side. This circuit is disposed downstream of two inputs 2, 3, to which the signal lines S1, S2 of the two electrodes 4, 5 of a bipolar cardiac catheter electrode 6 are connected.

Operational amplifiers 7, 8, which subject the input signals CARD or EMI conducted via the inputs 2, 3 to a measuring amplification, are disposed downstream of the inputs 2, 3. The outputs of the two preamplifiers 7, 8 are connected to the two inputs of a comparator 9, which emits an output signal that corresponds to the difference in the levels at its inputs. This output signal is evaluated by a downstream, phase-sensitive evaluation circuit 13. Cardiological scanning signals CARD and EMI interference signals EMI can thus be differentiated. If an EMI interference signal—i.e., a far-field signal—is detected, the output signal of the comparator 9 to be evaluated by the evaluation circuit 13 is a step function. In the event of a near-field signal, in which the signals present at the electrodes 4, 5 are bipolar cardiological signals, the evaluation circuit 13 must evaluate an output signal of the comparator 9 that appears to correspond, based on the fact that these near-field signals are out of phase. In short, the evaluation circuit 13 need only differentiate between a step function and a typical cardiological signal course.

The evaluation circuit is coupled via an amplification-control circuit 10 to the amplification-control inputs 11, 12 of the two preamplifiers 7, 8. The amplification-control circuit 10 is coupled to the evaluation circuit 13, as indicated by a solid-line arrow, so, when an interference signal is detected, the preamplifiers 7, 8 are actuated by corresponding control signals so as to minimize the comparator output signal. The latter can be looped through directly from the comparator 9 to the amplification-control circuit 10, as indicated by the dashed-line arrow between the comparator 9 and the amplification control 10.

The change in the preamplification at the preamplifiers 7, 8 is relevant for the implant function insofar as the value of the amplitude of the affected cardiological scanning signals is indicative for certain applications of the implant. For example, the amplitude value is significant with regard to threshold-value comparisons for detecting cardiac contractions. The change in the input amplification according to the invention minimizes interference signals, as is intended, but also influences the amplitude of the scanning signals. To effect a compensation, the change in the preamplification can be balanced out by an adaptation of the further processing of the comparator output signal. Bipolar cardiological scanning signals result as the output signal of the comparator. If a change occurs in the input amplification to eliminate interference signals, the output signal of the comparator is modified by the amplitude magnitude of the interference signals. This can be taken into consideration in the subsequent signal processing through a correspondingly-varied amplification or A/D conversion of the output signal of the comparator.

Unipolar signals result from the comparison of the input signals of an electrode and an indifferent pole, typically the implant housing. The compensation can be performed analogously to the above-described processes of bipolar scanning.

In summary, the method and the corresponding apparatus of the invention can detect cardiological signals, even in the presence of large EMI interference signals. These interference signals therefore no longer pose a problem for cardiological implants. The invention further permits the recognition of EMI interference signals, and their direct elimination from bipolar scanning signals. With a detection of EMI signals in accordance with the invention, other scanning signals, such as unipolar scanning signals of EMI interference signals, can be eliminated by a suitable circuit.

What is claimed is:

1. A method of discriminating between externally-radiated, electromagnetic interference signals and electro-medical scanning signals, particularly in input signals of cardiological implants such as cardiac pacemakers, defibrillators or the like, in neurological stimulus detectors, etc., the method comprising the following steps:

preamplification of the scanning signals by means of two preamplifiers (7, 8);

comparison of the preamplified scanning signals by a comparator (9); p1 phase-sensitive evaluation of the comparator output signal for differentiating between scanning signals (CARD) and interference signals (EMI); and feedback of the comparator output signal to an amplification control of the preamplifiers (7, 8) such that the comparator output signal is minimized when an interference signal is detected.

2. The method according to claim 1, wherein, for selecting interference signals, the comparator output signal is detected for step-function signals.

3. The method according to claim 1, wherein, in the detection of an interference signal and a corresponding change in the preamplification at the preamplifiers (7, 8), this change is compensated through an adaptation of the further processing of the comparator output signal.

4. An apparatus for executing the method according to claim 1, comprising a respective preamplifier (7, 8) for scanning signals (CARD);

a comparator (9), which is connected by its inputs to outputs of the preamplifiers (7, 8);

an amplification-control circuit (10), which is connected between the output of the comparator (9) and amplification-control inputs (11, 12) of the preamplifiers (7, 8); and an evaluation circuit (13), which is disposed upstream of the amplification-control circuit (10) for phase-sensitive evaluation of the comparator output signal to differentiate between scanning signals (CARD) and interference signals (EMI).

* * * * *